United States Patent [19]

Kamp

[11] Patent Number: 4,506,543

[45] Date of Patent: Mar. 26, 1985

[54] ANALYSIS OF SALT CONCENTRATIONS

[75] Inventor: Arthur J. Kamp, Oakley, Calif.

[73] Assignee: The Dow Chemical Company, Midland, Mich.

[21] Appl. No.: 506,072

[22] Filed: Jun. 20, 1983

[51] Int. Cl.³ ............................................ G01N 15/00
[52] U.S. Cl. ............................... 73/61 R; 73/861.04; 378/47
[58] Field of Search ................... 73/61 R, 53, 861.04; 250/573; 387/47, 53

[56] References Cited

U.S. PATENT DOCUMENTS

| | | | |
|---|---|---|---|
| 3,648,513 | 3/1972 | Patterson | 73/53 |
| 3,791,200 | 2/1974 | Hayre | 73/61 R |
| 3,982,126 | 9/1976 | von Alfthan | 378/47 |
| 4,228,353 | 10/1980 | Johnson | 378/47 |
| 4,266,425 | 4/1981 | Allport | 73/61 R |
| 4,352,288 | 10/1982 | Paap et al. | 73/61 R |

FOREIGN PATENT DOCUMENTS 2083908  3/1980  United Kingdom ................. 378/53

Primary Examiner—Gerald Goldberg
Assistant Examiner—Hezron Williams
Attorney, Agent, or Firm—Michael L. Glenn

[57] ABSTRACT

A method of determining the concentration of each of two salts in a liquid medium is disclosed. Sound velocity, X-ray absorption and temperature information are used to determine the respective concentrations.

8 Claims, 4 Drawing Figures

ANALYSIS OF SALT CONCENTRATIONS

BACKGROUND OF THE INVENTION

This invention relates to a method for determining the concentration of at least two salts in a liquid medium, wherein said salts exhibit different affects on X-ray absorption and sound velocity in the medium. In a preferred embodiment, this method determines the respective concentrations of (a) an ammonium or alkali metal hydroxide and (b) an ammonium or alkali metal halide, sulfite, sulfate, hypochlorite or hypobromite by measurement of sound velocity and X-ray absorption.

It is conventional in the prior art to determine the concentration of a salt in a liquid medium by one of a variety of "wet analysis" techniques. Titration methods for hydroxides are well established. Likewise, methods for analysis of halides via titration with silver nitrate are conventional. Specific titrimetric methods for determining concentration of many other compounds are known. See H. H. Willard et al, *Instrumental Methods of Analysis*, D. Van Nostrand Company Inc. (1965). However, such methods require automated or manual sample handling and are relatively slow.

Sound velocity measurements have recently emerged as a means for determining the concentration of solutes present in aqueous solutions. U.S. Pat. No. 3,648,513 describes the use of sound velocity measurements to determine the concentration of sodium chloride in underground bodies of water. Mokrousova et al, *Khim. Volokna*, 5, pp. 66-7 (1978), describe the use of sound velocity measurements to measure NaOH concentration. However, sound velocity measurements cannot accurately determine the concentration of more than one salt present in the aqueous solution wherein two or more of the salts affect the sound velocity.

Absorption of low-energy X-ray radiation has been used in the art to determine concentrations of certain materials. H. F. Liebhafsky et al, *X-Rays, Electrons and Analytical Chemistry*, pp. 127-170, Wiley-Interscience (1972). This analytical technique also does not permit accurate determination of concentrations in multicomponent solutions where more than one component abosrbs X-rays.

SUMMARY OF THE INVENTION

The invention is a method for determining the respective concentrations in a liquid medium of (a) a first salt component and (b) a second salt component, wherein for components "a" and "b" the following is true:

$$\frac{dV_a}{d[a]} / \frac{dV_b}{d[b]} \neq \frac{dA_a}{d[a]} / \frac{dA_b}{d[b]}.$$

The derivative $dV_i/d[i]$ relates the change in sound velocity in the liquid medium to the concentration of component i. The derivative $dA_i/d[i]$ relates the change in X-ray absorption of the liquid medium to the concentration of component i.

$V_i$ is the sound velocity in the liquid medium in the presence of component i at a specific concentration, [i]. $A_i$ is the absorption of low energy X-rays in the liquid medium in the presence of component i at a specific concentration, [i]. Of course, component i can be either the salt "a" or "b" as described above.

In this method the sound velocity in the liquid medium is measured. The temperature of the solution during the sound velocity measurement is also determined. The absorption of a beam of low energy X-rays by the medium is also measured. The concentration of components "a" and "b" is then calculated from empirical formulae relating sound velocity at the measured temperature and X-ray absorption to respective concentrations of "a" and "b" in the liquid medium.

DETAILED DESCRIPTION OF THE INVENTION

The subject method is useful in determining the respective concentrations of salts having different relative affects on X-ray absorption and sound velocity. The greater the difference between the quantities $$\left(\frac{dV_a}{d[a]} / \frac{dV_b}{d[b]}\right) \text{ and } \left(\frac{dA_a}{d[a]} / \frac{dA_b}{d[b]}\right),$$

generally the better the accuracy of the subject method in determining the respective concentrations of "a" and "b". Preferably, these quantities differ by at least a factor of 2, more preferably at least a factor of 5 and most preferably at least a factor of 10. In other words, the lesser of these two quantities would need to be multiplied by the aforementioned factors to equal the other quantity.

One of ordinary skill in that art with the guidance of instruction provided herein can readily identify combinations of salts subject to the instant method for determining their respective concentrations. In general for both "a" and "b", alkali metal or ammonium salts, particularly sodium salts, are most conveniently and accurately analyzed to determine their concentration by the subject method. Salts with the following anions are of particular interest: $Cl^-$, $Br^-$, $F^-$, $I^-$, $S^=$, $SO_3^=$, $HSO_3^-$, $HSO_4^-$, $SO_4^=$, $CO_3^=$, $HCO_3^-$, $OCl^-$, $OBr^-$ and $OH^-$.

In general, the preferred salts referred to as component (a) exhibit a relatively rapid increase of sound velocity in the solution as their concentration increases, but are relatively weak in the absorption of X-rays when compared with component (b), i.e., $$\frac{dV_a}{d[a]} > \frac{dV_b}{d[b]} \text{ and } \frac{dA_a}{d[a]} < \frac{dA_b}{d[b]}.$$

Especially preferred salts of type "a" are NaOH, NH$_4$OH and KOH, most preferably NaOH.

In general, the preferred salts described as component (b) increase the velocity of sound to a lesser degree with increasing concentration, but are relatively strong absorbers of X-rays compared to component (a). Especially preferred salts of this type are NaCl, NH$_4$Cl, KCl and NaOCl, most preferably NaCl.

The sound velocity in the medium is increased significantly by hydroxide and carbonate anions, while these anions are relatively poor absorbers of X-rays. Accordingly, hydroxide and carbonate anions are preferred in the salts referred to herein as component (a).

Anions containing atoms of comparatively high atomic weight are in general better absorbers of X-rays. Accordingly, preferred anions in salts referred to as component (b) are those containing sulfur atoms, such as sulfite, sulfate, sulfide, or halogens, such as chloride, bromide, iodide, hypochlorite and hypobromite.

Figure 3:
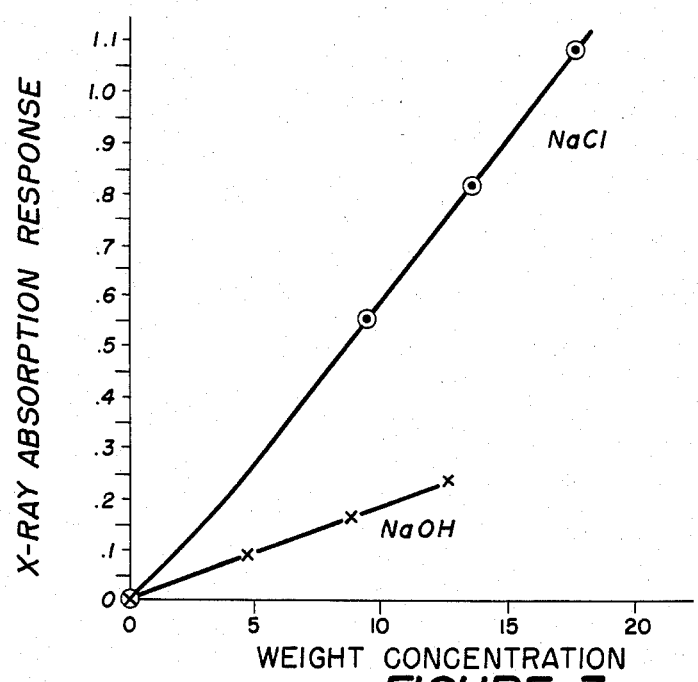
FIG. 3 is an illustrative graphical representation of how the X-ray absorption of NaOH and NaCl varies with the concentration of these compounds in an aqueous solution.
Figure 4:
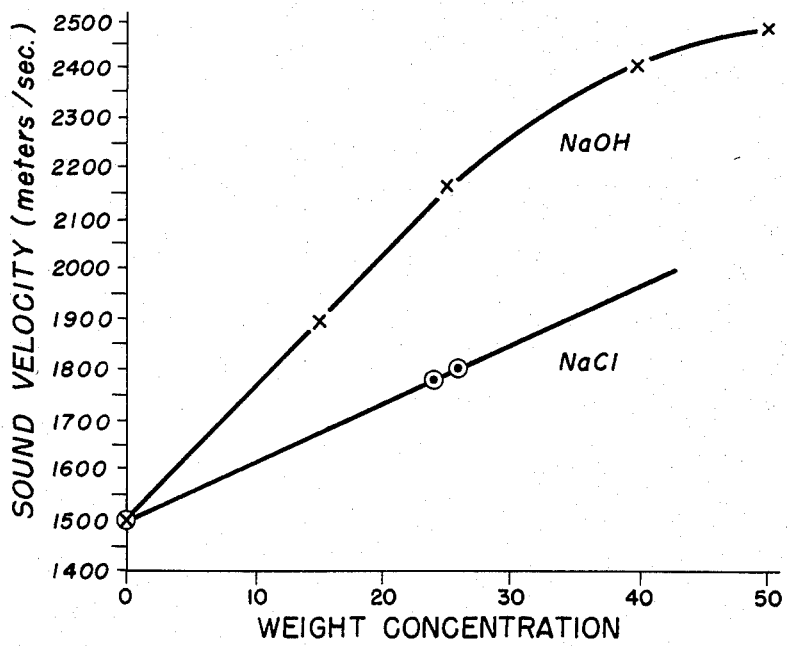
FIG. 4 is an illustrative graphical representation of how sound velocity in an aqueous solution varies as a function of the concentration of NaOH and NaCl.

FIGS. 3 and 4 illustrate the respective affects of NaCl and NaOH on sound velocity (at 25° C.) and X-rays absorption as a function of concentration. Typically, at lower salt concentrations (less than about 30 weight percent) both sound velocity and X-ray absorption vary monotonically as a function of concentration. At these lower concentrations for NaCl and NaOH as depicted in FIGS. 3 and 4.

$$\frac{dV_{NaCl}}{d[NaCl]} = 11 \frac{\text{meters/second}}{\text{wt. \% NaCl}} ; \frac{dV_{NaOH}}{d[NaOH]} =$$

$$27 \frac{\text{meters/second}}{\text{wt. \% NaOH}} ; \frac{dA_{NaCl}}{d[NaCl]} = 0.132 \frac{\text{Abs. Units}}{\text{wt. \% NaCl}} \text{ and}$$

$$\frac{dA_{NaOH}}{d[NaOH]} = 0.019 \frac{\text{Abs. Units}}{\text{wt. \% NaOH}}.$$

Absorption (Abs.) units are dimensionless units related to the diminished intensity of X-ray radiation due to absorption. Sound velocity generally increases with salt concentration, as does X-ray absorption. The affect of a combination of these salts on both sound velocity and X-ray absorption is essentially additive; i.e., the affect of the two components together is approximately the sum of their independent affects on both sound velocity and X-ray absorption.

It is preferred that the liquid medium contains only a single salt for component (a) and a different single salt for component (b). The presence of only two salts permits the determination of the concentrations of each salt by the subject method.

Where either component (a) or (b) comprises more than one salt, it is not possible to determine the concentrations of the individual salts making up the component unless the concentrations of all but one of these salts is already known. However, since the individual salts in a single category, whether (a) or (b), frequently show similar X-ray absorption and sound velocity affects, the cumulative concentrations of the salts in each category can be determined with some accuracy. Some pairs of salts, such as NaCl and NaOCl, exhibit very similar responses, in which case the total concentration of this salt pair can be determined with considerable accuracy (often within 5%) in the presence of a third salt having dissimilar affects, such as NaOH. On the other hand, where NaCl and NaOCl are the only salts present, their affects on both X-ray and sound velocity are sufficiently similar that their respective concentrations cannot be determined with great accuracy. Other salt combinations, such as NaCl and NaBr, differ sufficiently in their affects in X-ray absorption and sound velocity that concentrations of this combination of salts cannot be determined very accurately by the subject method alone in the presence of a dissimilar third salt. In such instances it may be necessary to determine the concentration of one of the salts present by other analytical techniques.

In general, sound velocity in a liquid medium also increases with temperature. Accordingly, it is also important to measure the temperature of the medium when sound velocity measurements are made. Of course, temperature of the medium need not be measured if it is maintained at a predetermined value. Generally, the temperature at which sound velocity measurements are actually made is not critical so long as calibrations of salt concentration and sound velocity have been made at that temperature and the medium remains a liquid. Temperatures from about 25° C. to about 80° C. are preferred for measurements.

Temperature also has a minor affect on X-ray absorption. However, this temperature affect is so minor that it can generally be neglected.

Pressure can also affect the sound velocity measured, but this affect is relatively small and usually can be discounted. Conveniently, the sample is at atmospheric pressure when analyzed.

The solvent in the liquid medium can be any solvent which exhibits a predictable change in the velocity of sound and X-ray absorption dependent on the concentrations of the salts dissolved therein. Water is especially preferred as a solvent. The preferred aqueous medium can contain minor amounts of alkanols or other co-solvents which do not interfere with sound velocity or X-ray absorption measurements. Of course, for maximum accuracy sound velocity and X-ray absorption measurements should be calibrated in the same medium as the sample.

Figure 1:
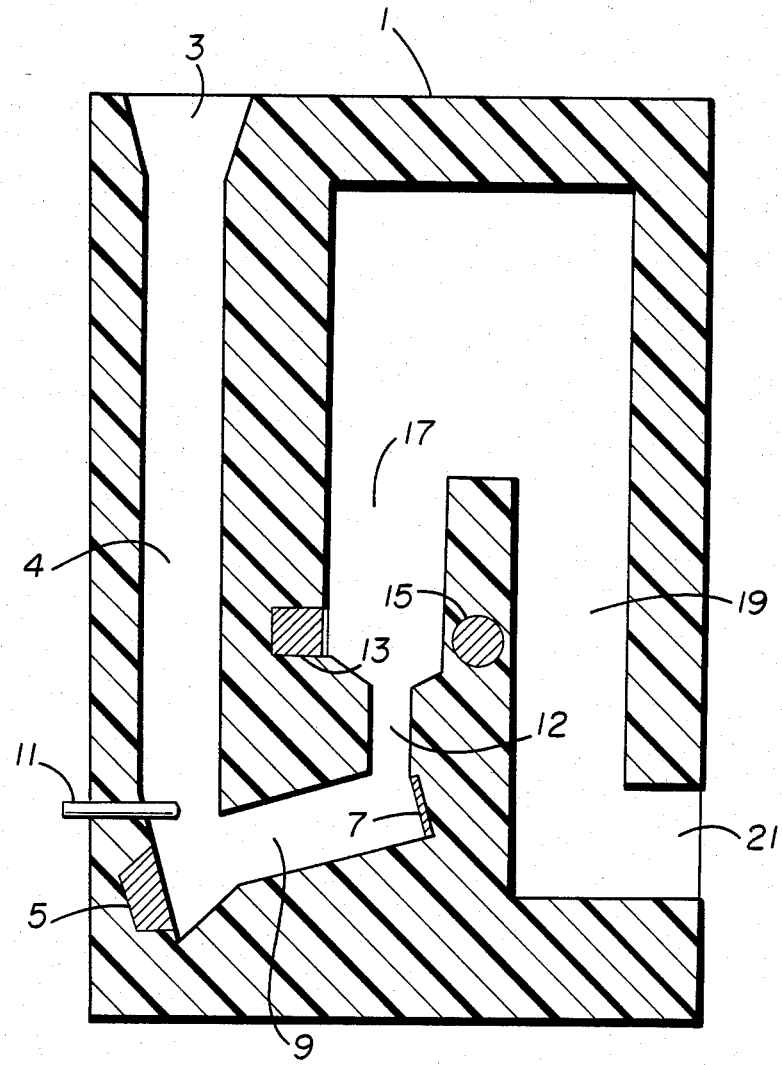
FIG. 1 is a cross-sectional view of a preferred apparatus which can be used in the performance of the subject method.

The apparatus used in the instant method can be assembled from commercially available components and materials. FIG. 1 depicts a preferred configuration of such an apparatus. Minor components serving obvious functions, such as shielding and seals, as well as electrical connections have not been depicted for sake of clarity in the drawing. The apparatus includes a housing 1 fabricated from a material resistant to the liquid medium and the salts therein, e.g., high-density polyethylene is a preferred housing material in the case of aqueous solutions of NaOH and NaCl. In the housing 1 is formed a sample inlet 3 which communicates through a channel 4 with a chamber 9 for sound velocity measurement. The sound velocity chamber 9 is angled at about 15° from horizontal to minimize interference from gas bubbles. At one end of the chamber 9 is a sonic transducer 5, at the opposite end a sonic reflector 7 and situated nearby is a temperature detector 11. It is also possible to use a second sonic transducer in place of the sonic reflector 7. The sound velocity chamber 9 communicates through a passage 12 with an X-ray absorption chamber 17, which has at one side a low energy X-ray source 13 and at the other side an X-ray detector 15. The X-ray absorption chamber 17 communicates through a passage 19 with a sample outlet 21.

It has been found that the apparatus depicted in FIG. 1, when appropriately sized, can be used for rapid sequential analysis of relatively small volumes of samples (less than 100 milliliters). Each successive sample typically displaces essentially all residue of previous samples of similar composition. Consequently, accurate analyses are possible without cleaning the apparatus between samples. Analysis can be initiated automatically upon sample introduction or manually.

This same apparatus can also be readily adapted for analysis of a continuous sample stream at frequent intervals (30 seconds or less) in a manner apparent to one of ordinary skill in the art. The sound velocity measurement, X-ray detection and temperature measurement instrumentation can be conveniently disposed on a section of straight pipe which serves the same function as channels 4, 12 and 19 and chambers 9 and 17 in FIG. 1. Of course, the sonic transducer and reflector (or second sonic transducer) should be disposed on opposite walls of the pipe, as should the X-ray source and detector. Desirably all instrumentation is in close proximity to avoid corrections that might otherwise be necessary to minimize errors attributable to local variations in concentration.

Figure 2:
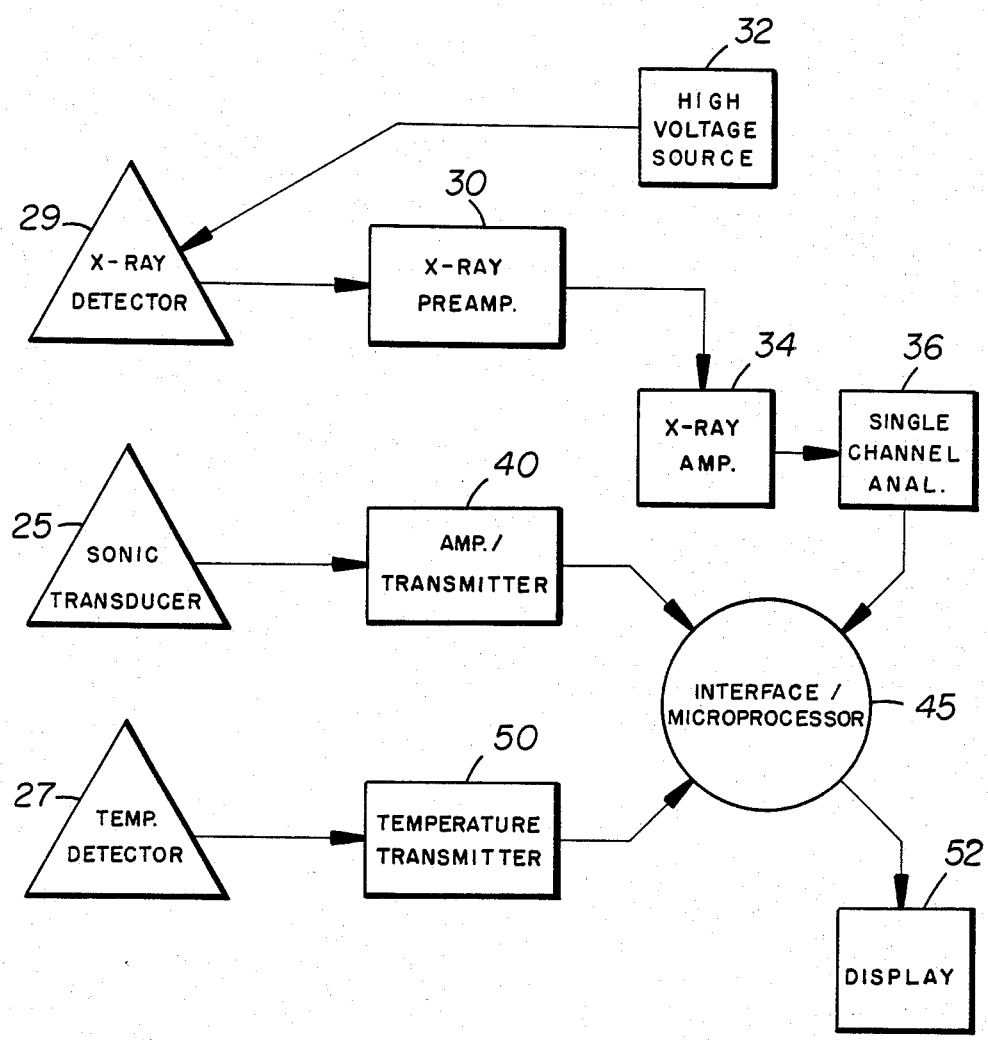
FIG. 2 is a block diagram depicting components and circuit elements used in determining temperature, sound velocity, X-ray absorption and concentrations of "a" and "b" in the solution.

FIG. 2 depicts schematically electronics associated with the apparatus shown in FIG. 1. The sonic transducer 25, when stimulated by an acoustic pulse, relays an electrical signal to the amplifier/transmitter 40. The amplifier/transmitter 40 amplifies the signal, determines the elapsed time between acoustic pulse generation and detection of the pulse by the transducer 25. The transmitter 40 relays an electrical signal proportional to the velocity of sound through the medium traversed between the source of the acoustic pulse and the transducer 25 to the interface/microprocessor 45.

The temperature detector 27 generates an electrical signal proportional to the temperature of the medium it is in contact with and relays this signal to the temperature transmitter 50. The transmitter 50 processes and relays an electrical signal to the interface/microprocessor 45 conveying the desired temperature information.

The high voltage source 32 energizes the X-ray detector 29. (Other conventional X-ray detectors can also be used.) The weak electrical signal from the detector is amplified by a preamplifier 30. The amplified signal is conducted to an amplifier 34 and from there to a single channel analyzer 36 for processing. The digital signal from the converter 36 is sent to the interface microprocessor 45.

The interface/microprocessor 45 contains in its memory values corresponding to the X-ray absorption and sound velocity response of components (a) and (b) in the liquid medium of the sample at various concentrations and temperatures. The microprocessor 45 is programmed to determine from X-ray absorption, sound velocity and temperature measurements the concentrations of "a" and "b" using the X-ray absorption and sound velocity calibrations in its memory. The concentrations calculated are shown in the display 52.

In essence the program to determine concentrations of "a" and "b" involves the solution of the two equations $$V_m = \frac{dV_a}{d[a]} [a] + \frac{dV_b}{d[b]} [b] + V_o$$

$$A_m = \frac{dA_a}{d[a]} [a] + \frac{dA_b}{d[b]} [b] + A_o$$

wherein the measured sound velocity, $V_m$, and measured X-ray absorption, $A_m$, are determined as described herein and the sound velocity at zero salt concentration, $V_o$, the X-ray absorption at zero salt concentration, $A_o$, and all other factors except the concentration of "a", [a], and "b", [b], are available in memory.

In instances where there are compounds present in the liquid medium other than components "a" and "b" which contribute to sound velocity or X-ray absorption, as was noted previously the concentration of these compounds should be determined by other analytical techniques. The contribution of the interfering compound to sound velocity and X-ray absorption can then be determined and subtracted from the measured values. The concentrations of "a" and "b" are then determined as described above.

The sonic transducer, reflector and amplifier/transmitter described herein are available commercially. MAPCO INC. markets transducers and reflectors as units as well as amplifier/transmitters for use in sonic velocity measurements. It is desirable, that the transducer be sensitive to only the first large received pulse to minimize false readings due to undesired reflections. The transducer is available with heads fabricated from a variety of materials. Of course, the head should be selected from a material not deleteriously affected by the medium it contacts.

The temperature detector can be any conventional temperature measuring device compatible with the sample medium. Resistance temperature detectors are preferred because of their sensitivity, reliability and availability. The electronics associated with such detectors are available commercially.

The X-ray source is advantageously a low-energy source, preferably 5–1000 KeV (kilo electron volt). A convenient source of such X-rays is a target material irradiated by a radioisotope to produce X-rays of the desired energy. One preferred combination is a tin target irradiated by an annular americium-241 source. The target is disposed so that X-rays scattered from the target pass through the sample to the detector. This combination can be tailored to provide X-rays of an energy which will be absorbed to a significant degree in concentrated solutions of interest but are not completely absorbed. The americium-241 has a very long half-life so the intensity of the X-rays remains relatively constant and updating of the microprocessor memory to reflect changes in the intensity of the X-rays in a salt-free solution is not usually required. The radioisotope should be shielded to prevent irradiation of the sample as well as the operating environment. Other sources of X-rays, such as X-ray tubes are also operable.

Any conventional X-ray detector of suitable sensitivity can be employed in the determination of X-ray intensity. Gas-filled ionization detectors are generally preferred. Electronic circuits for amplifying and processing the resulting signal are known in the art. See H. A. Liebhafsky et al, *X-Rays, Electrons and Analytical Chemistry*, pp. 58–170, Wiley-Interscience (1972).

The subject method exhibits utility in many diverse applications. The concentration of both NaOH and NaCl in aqueous effluent from electrochemical cells can be determined in seconds. A precision (at 95% confidence level) of ±2 grams/liter NaOH and ±5 grams/liter NaCl has been observed in such applications. If the effluent is monitored continuously by the subject method, an early indication of electrochemical cell upset or inefficiencies is afforded. The flow rate of effluent and current used by electrochemical cells can be monitored separately by conventional techniques and the concentration of NaCl and NaOH in the cell effluent taken with this other data provides a continuous indication of current efficiency in caustic production. The measurement of caustic current efficiency is of great benefit in optimizing cell efficiency.

Alkali metal hydroxides or carbonates are frequently used to scrub chlorine or acids from gases. The subject method can provide a rapid indication of the concentration of alkali metal hydroxide or carbonate remaining in the scrubbing liquor. For example the scrubbing of chlorine with aqueous NaOH proceeds by the reaction:

$$2NaOH + Cl_2 \rightarrow NaCl + NaOCl + H_2O.$$

Because NaCl and NaOCl exhibit very similar sound velocity and X-ray absorption affects, the remaining concentration of NaOH in the scrubbing liquor can be readily determined by the subject method.

The following examples are presented to illustrate but not limit the scope of the subject invention.

EXAMPLES 1–17

A bench-top analyzer similar in design to that depicted in FIG. 1 was used to successively determine the NaOH and NaCl concentration in sixteen aqueous 100 milliliter samples at 25° to 55° C. Portions of each sample were also titrated by conventional methods to determine the concentration of NaOH and NaCl. The results of the analyses and titrations are tabulated in Table I.

TABLE I

| Example No. | Bench-Top Analyzer | | Titration | |
|---|---|---|---|---|
| | [NaCl] | [NaOH] | [NaCl] | [NaOH] |
| 1 | 227 | 100 | 229 | 100 |
| 2 | 181 | 59 | 182 | 61 |
| 3 | 183 | 125 | 182 | 62 |
| 4 | 213 | 123 | 211 | 124 |
| 5 | 156 | 114 | 157 | 113 |
| 6 | 160 | 101 | 159 | 102 |
| 7 | 198 | 103 | 197 | 102 |
| 8 | 190 | 113 | 192 | 112 |
| 9 | 172 | 80 | 171 | 79 |
| 10 | 229 | 82 | 229 | 82 |
| 11 | 227 | 60 | 227 | 60 |
| 12 | 143 | 124 | 144 | 123 |
| 13 | 138 | 139 | 139 | 138 |
| 14 | 173 | 160 | 173 | 161 |
| 15 | 136 | 148 | 136 | 149 |
| 16 | 135 | 163 | 134 | 163 |
| 17 | 176 | 139 | 176 | 139 |

What is claimed is:

1. A method for determining the respective concentrations in a liquid medium of (a) a first salt component and (b) a second salt component, said method comprising the steps of:
   (1) measuring sound velocity in the liquid medium;
   (2) measuring absorption of low-energy X-rays by the liquid medium;
   (3) determining temperature of the liquid medium in the region where sound velocity is measured; and
   (4) calculating the concentrations of (a) and (b) from predetermined empirical formulae relating sound velocity at the measured temperature and X-ray absorption in the liquid medium to the concentrations of (a) and (b).

2. The method as described in claim 1, wherein either component (a) or (b) comprise more than one salt and all of the salts comprising (a) exhibit sufficiently similar concentration dependent affects on sound velocity and X-ray absorption and all of the salts comprising (b) exhibit sufficiently similar concentration dependent affects on sound velocity and X-ray absorption, such that said method determines the total concentrations of the salts in both (a) and (b) to an accuracy of about 5 percent of the molar concentration.

3. The method as described in claim 1 wherein the liquid medium comprises at least one third component, the concentration of which is determined separately by conventional methods, and the affect of the third component on sound velocity and X-ray absorption is subtracted from the measured values before calculating the concentration of (a) and (b).

4. The method as described in claim 1 wherein the liquid medium is water.

5. The method as described in claim 4 wherein (a) is NaOH and (b) is NaCl.

6. The method as described in claim 4 wherein (a) is NaOH and (b) is a mixture of NaCl and NaOCl.

7. The method as described in claim 1 wherein $$\left( \frac{dV_a}{d[a]} \bigg/ \frac{dV_b}{d[b]} \right) \text{ differs from } \left( \frac{dA_a}{d[a]} \bigg/ \frac{dA_b}{d[b]} \right)$$

by at least a factor of 5, wherein $V_a$ is the sound velocity in the liquid medium in the presence of the first salt component at concentration, [a], $V_b$ is the sound velocity in the liquid medium in the presence of the second salt component at a concentration, [b], $A_a$ is the absorption of low-energy X-rays in the liquid medium in the presence of the first salt component at a concentration, [a], and $A_b$ is the absorption of low energy X-rays in the liquid medium in the presence of the second salt component at a concentration, [b].

8. An apparatus for measuring the concentration of at least two components dissolved in a liquid medium comprising a housing which includes a sample inlet opening and sample outlet opening, disposed between said sample inlet and outlet openings in no specific sequence are (i) a means for measuring sound velocity in the medium, (ii) a means for determining temperature of the medium and (iii) means for measuring X-ray absorption in the medium, and further comprising an information processor programmed to determine the respective concentrations of the first and second components in the medium from sound velocity, temperature and X-ray absorption data.

* * * * *